United States Patent
Ahmed et al.

(10) Patent No.: US 11,422,122 B2
(45) Date of Patent: Aug. 23, 2022

(54) MEASURING WATER CONTENT OF PETROLEUM FLUIDS USING DRIED PETROLEUM FLUID SOLVENT

(71) Applicant: Saudi Arabian Oil Company, Dhahran (SA)

(72) Inventors: Elaf A. Ahmed, Dhahran (SA); Sebastien A. Duval, Dhahran (SA); Simone Less, Dhahran (SA); Ali S. Aldossary, Al Khubar (SA)

(73) Assignee: Saudi Arabian Oil Company, Dhahran (SA)

( * ) Notice: Subject to any disclaimer, the term of this patent is extended or adjusted under 35 U.S.C. 154(b) by 149 days.

(21) Appl. No.: 16/907,565

(22) Filed: Jun. 22, 2020

(65) Prior Publication Data

US 2021/0396731 A1 Dec. 23, 2021

(51) Int. Cl.
*G01N 33/24* (2006.01)
*G01N 1/18* (2006.01)
(Continued)

(52) U.S. Cl.
CPC ............ *G01N 33/246* (2013.01); *G01N 1/18* (2013.01); *G01N 1/2035* (2013.01); *G01N 1/405* (2013.01);
(Continued)

(58) Field of Classification Search
CPC ........ G01N 33/18; G01N 1/18; G01N 1/2035; G01N 1/405; G01N 2001/1031;
(Continued)

(56) References Cited

U.S. PATENT DOCUMENTS 4,034,219 A 7/1977 Louden et al.
4,157,247 A 6/1979 Collins, III et al.
(Continued)

FOREIGN PATENT DOCUMENTS

AU 2004204512 7/2004
CN 109696372 4/2019
(Continued)

OTHER PUBLICATIONS

Vaisala, Vaisala Humicap sensor for measuring moisture in oil, 2012 (Year: 2012).*
(Continued)

*Primary Examiner* — John Fitzgerald
*Assistant Examiner* — Truong D Phan
(74) *Attorney, Agent, or Firm* — Fish & Richardson P.C.

(57) ABSTRACT

To measure water content of liquid hydrocarbon using dried liquid hydrocarbon solvent, a liquid hydrocarbon sample is received from a flowline carrying the liquid hydrocarbon. The liquid hydrocarbon sample includes liquid hydrocarbon and liquid water at a concentration greater than a water saturation level. The liquid hydrocarbon sample is split into a first portion and a remainder portion. The first portion is dried to remove liquid water in the first portion. The remainder portion is mixed with the dried first portion causing the concentration of liquid water in a mixture of the remainder portion and the dried first portion to be below the water saturation level. After mixing the remainder portion with the dried first portion, a water content in the liquid hydrocarbon sample is determined.

18 Claims, 4 Drawing Sheets

(51) Int. Cl.
  *G01N 1/20* (2006.01)
  *G01N 1/40* (2006.01)
  *G01N 27/22* (2006.01)
  *G01N 1/10* (2006.01)

(52) U.S. Cl.
  CPC ... *G01N 27/223* (2013.01); *G01N 2001/1031* (2013.01)

(58) Field of Classification Search
  CPC .............. G01N 27/223; G01N 33/246; G01N 33/2847; G01N 33/2833; G01N 33/1833; G01N 2015/0668; G01N 31/168; G01N 2030/8854; G01N 33/28; G01N 33/241; G01N 33/2823
  See application file for complete search history.

(56) References Cited

U.S. PATENT DOCUMENTS

| | | |
|---|---|---|
| 4,466,946 A | 8/1984 | Goddin, Jr. et al. |
| 4,581,134 A | 4/1986 | Richter, Jr. et al. |
| 4,589,896 A | 5/1986 | Chen et al. |
| 4,701,187 A | 10/1987 | Choe |
| 4,717,407 A | 1/1988 | Choe et al. |
| 4,797,550 A | 1/1989 | Nelson et al. |
| 5,035,065 A | 7/1991 | Parkinson |
| 5,067,345 A | 11/1991 | Mougne |
| 5,259,239 A | 11/1993 | Gaisford |
| 5,294,553 A | 3/1994 | Kawahara |
| 5,381,002 A | 1/1995 | Morrow |
| 5,401,300 A | 3/1995 | Lokhandwala et al. |
| 5,407,466 A | 4/1995 | Lokhandwala et al. |
| 5,407,467 A | 4/1995 | Lokhandwala et al. |
| 5,454,258 A * | 10/1995 | Capuano ............ G01N 33/0011 73/61.41 |
| 5,632,803 A | 5/1997 | Stoner |
| 5,837,032 A | 11/1998 | Moll et al. |
| 6,179,900 B1 | 1/2001 | Behling et al. |
| 6,361,582 B1 | 3/2002 | Pinnau et al. |
| 6,656,249 B1 | 12/2003 | Buisnnan |
| 6,896,717 B2 | 5/2005 | Pinnau et al. |
| 7,469,188 B2 | 12/2008 | Wee |
| 8,323,392 B2 | 12/2012 | Jones |
| 8,722,003 B1 | 5/2014 | Avagliano et al. |
| 8,828,121 B1 | 9/2014 | He et al. |
| 9,157,035 B1 | 10/2015 | Ball, IV et al. |
| 9,181,499 B2 | 11/2015 | Mason et al. |
| 9,244,017 B2 | 1/2016 | Cadieux, Jr. et al. |
| 9,448,221 B2 | 9/2016 | Duval et al. |
| 10,024,835 B2 | 7/2018 | Sreekumar |
| 10,197,545 B2 | 2/2019 | Sreekumar et al. |
| 10,386,284 B2 | 8/2019 | Zhang |
| 2005/0217479 A1 | 10/2005 | Hale et al. |
| 2010/0264014 A1 | 10/2010 | Mignon et al. |
| 2012/0111051 A1 | 5/2012 | Kulkarni et al. |
| 2012/0168154 A1 | 7/2012 | Chinn et al. |
| 2012/0323059 A1 | 12/2012 | Liu et al. |
| 2013/0110411 A1 | 5/2013 | Black et al. |
| 2015/0240717 A1 | 8/2015 | Starcher et al. |
| 2015/0290575 A1 | 10/2015 | Rothermel et al. |
| 2015/0298972 A1 | 10/2015 | Ballaguet et al. |
| 2016/0121258 A1 | 5/2016 | First |
| 2016/0228813 A1 | 8/2016 | Schwartz |
| 2017/0312682 A1 | 11/2017 | Keller |
| 2017/0320736 A1 | 11/2017 | Voss et al. |

FOREIGN PATENT DOCUMENTS

| | | |
|---|---|---|
| EP | 684066 | 11/1995 |
| EP | 2932239 | 10/2015 |
| GB | 2336668 | 2/2003 |
| GB | 0908527 | 5/2009 |
| WO | WO 2013068320 | 7/2013 |
| WO | WO 2018129228 | 7/2018 |
| WO | WO 2018236644 | 12/2018 |

OTHER PUBLICATIONS

Amo et al., "Low-Quality Natural Gas Sulfur Removal/Recovery," Membrane Technology and Research, DOE Report DE-AC21-92MC28133—01, Jan. 29, 1998, 107 pages.

Aschoundong et al., "Silane Modification of Cellulose Acetate Dense Films as Materials for Acid Gas Removal Macromolecules," American Chemical Society (ASC) Publications, Macromolecules 46:14 (5584-5594), Jul. 9, 2013, 11 pages.

ASTM International, "Standard test method for dimer/trimer of chlorotrifluoroethylene (S-316) recoverable oil and grease and nonpolar by Infared determination," Designation D7066-04, ASTM International, 2007 (reapproved 2017), 9 pages.

ASTM International, "Standard test method for oil and grease (fluorocarbon extractable substances) by gravimetric determination," Designation D4281-95, an American Standard, ASTM International, 1995 (reapproved 2005), 6 pages.

ASTM International, "Standard test method for oil and grease and petroleum hydrocarbons in water," Designation D3921-85, 1985 (reapproved 1990), ASTM International, 5 pages.

Belov et al., "Gas transport and free volume in hexafluoropropylene polymers," Journal of Membrane Science 383: 70-77, Nov. 2011, 8 pages.

Ben-Shebil, "Effect of heat of adsorption on the adsorptive drying of solvents at equilibrium in a packed bed of zeolite," Chemical Engineering Journal, 74:3 (197-204), Jul. 1999, 8 pages.

Bernardo et al., "Gas transport properties of Pebax/room temperature ionic liquid gel membranes" Separation and Purification Technology 97: 73-82, Sep. 2012, 13 pages.

Bhide et al., "Hybrid processes for the removal of acid gases from natural gas," Journal of Membrane Science 140:1 (27-49), Mar. 4, 1998, 2 pages, Abstract Only.

Chatterjee et al., "Poly(ether urethane) and poly (ether urethane urea) membranes with high $H_2S/CH_4$ selectivity," Journal of Membrane Science 135:99 (99-106), Nov. 1997, 8 pages.

Cirne et al., "Methods for Determination of Oil and Grease Contents in Wastewater from the Petrolem Industry," Chemistry and Chemical Technology 10:4, 2016, 8 pages.

EPA "Oil and Grease (Spectrophotometric, Infrared)," Method # 413.2, Storet No. 00560, Issued in 1974, Editorial revision 1978, Standard test method for Oil and grease analysis using Freon extraction and IR absorbance without the Freon extract being treated by silica gel, 3 pages.

EPA, "Method 1664, Revision A: N-Hexane Extractable Material (HEM; Oil and Grease) and Silica Gel Treated N-Hexane Extractable Material (SGT-HEM; Non-polar material) By Extraction and Gravimetry," United States Environmental Protection Agency, Office of Water, Washington D.C., EPA-821-R-98-002, PB99-121949, Feb. 1999, 28 pages.

EPA, "Method 1664, Revision B: N-Hexane Extractable Material (HEM; Oil and Grease) and Silica Gel Treated n-Hexane Extractable Material (SGT-HEM; Non-polar Material) by Extraction and Gravimetry," United States Environmental Protection, Office of Water Agency, EPA-821-R-10-001, Feb. 2010, 35 pages.

EPA, "Oil and Grease (Gravimetric, Separatory Funnel Extraction)," Method # 413.1, Storet No. 00556, Issued in 1974, Editorial revision 1978, Standard test method for oil and grease using gravimetric determination, approved for NPDES, 3 pages.

EPA, "Petroleum Hydrocarbons (Spectrophotometric, Infrared)," Method # 418.1, Storet No. 45501, Issued in 1978, Petroleum Hydrocarbons, 3 pages.

Gabrus et al., "Experimental studies on 3 A and 4A zeolite molecular sieves regeneration in TSA process: Aliphatic alcohols dewatering-water desorption," Chemical Engineering Journal 259: 232-242, Jan. 2015, 11 pages.

Glasoe et al, "Solubility of water and deuterium oxide in carbon tetrachloride, toluene, and cyclohexane at various temperatures," Journal of Chemical and Engineering Data, 17:1 (66-68), 1972, 3 pages.

Hibbard and Schalla, "NACA Research Memorandum: Solubility of Water in Hydrocarbons," National Advisory Committee for Aeronautics, Washington, Jul. 10, 1952, 27 pages.

(56) References Cited

OTHER PUBLICATIONS

International Standard, "Water quality—Determination of Hydrocarbon Oil Index—Part 2: Method Using Solvent Extraction and Gas Chromatography," ISO 9377-2, First edition, Oct. 15, 2000, 24 pages.
International Standard, "Water Quality—Sampling—Part 3: Guidance on the Preservation and Handling of Water Samples," ISO 5667-3, Third Edition, Dec. 15, 2003, 38 pages.
IP, "Determination of the oil content of effluent water—extraction and infra-red spectrometric method," IP 429/98, Oil in Water, 2012, 5 pages.
Jansen et al., "On the unusual solvent and the effect on the gas transport in perfluorinated Hyflon AD Membranes," Journal of Membrane Science 287:1 (132-137), Jan. 2007, 6 pages.
Johnson et al, "The Molecular Complexity of Water in Organic Solvents Part II," J. Chem. Soc. A, Inorganic Phys. Theoretical 77-78, 1966, 2 pages.
Kirchnerová et al, "The Solubility of Water in Low-Dielectric Solvents," Can. J. Chem 54:24 (3909-3916), Aug. 26, 1976, 8 pages.
Knauss et al, "The solubility of p-xylene in water as a function of temperature and pressure and calculated thermodynamic quantities," Geochimica et Cosmochimica Acta vol. 59:12 (2443-2448), Jun. 1995, Mar. 1995, 6 pages.
Ko et al., "Analysis of purge gas temperature in cyclic TSA process," Pergmon, Chemical Engineering Science 57:1 (179-195), Jan. 2002, 17 pages.
Kraftschik et al., "Dense film polyimide membranes for aggressive sour gas feed separations," Journal of Membrane Science 428: 608-619, Feb. 1, 2013, 12 pages.
Lallemand et al., "Extending the treatment of highly sour gases: cryogenic distillation," Digital Refining: Processing, Operations & Maintenance, PTQ Q1, Jan. 2014, 8 pages.
Lallemand et al., "Highly sour gas processing: Bulk removal with SPREX Process," IPTC-10581-MS, presented at the SOGAT Conference, International Petroleum Technology Conference, Nov. 2005, 18 pages.
Lallemand et al., "Solutions for the treatment of highly sour gases," Digital Refinding: Processing, Operations & Maintenance, Gas, Apr. 2012, 14 pages.
Lockhart, "Sour oil and gas management: 3.3," New Upstream Technologies, vol. III/New Developments: Energy, Transport, Sustainability Encyclopedia of Hydrocarbons, 2007, 34 pages.
Lokhandwala et al., "Membrane separation of nitrogen from natural gas: A case study from membrane synthesis to commercial deployment," Journal of Membrane Science 346: 270-279, Jan. 2010, 10 pages.
Merkel and Toy, "Comparison of Hydrogen Sulfide Transport Properties in Fluorinated and Nonfluorinated Polymers," Macromolecules 39:22 (7591-7600), Sep. 2006, 10 pages.
Michell Instruments (online), "Impedance," Impedance Products, URL: <http://www.michell.com/uk/technology/impedence.htm> retrieved Sep. 9, 2019, available on or before Jun. 2019, 2 pages.
Odberg et al, "Studies of water in organic solvents using NMR and partition techniques-II Di-isopropyl ether, dibutyl phthalate and chloroform," Journal of Inorganic and Nuclear Chemistry 34:8 (2605-2616), Aug. 1972, Mar. 18, 1971, 12 pages.
Robeson, "The upper bound revisited," Journal of Membrane Science 320 (390-400), Jul. 15, 2008, 11 pages.
Rufford et al., "The removal of CO2 and N2 from natural gas: A review of conventional and emerging process technologies," Journal of Petroleum Science and Engineering 94-95: 123-154, Sep. 2012, 32 pages.
Sensorland.com (online), "Impedance Moisture Sensor Technology," How Sensors work—Moisture Sensors, retrieved from URL: <http://www.sensorland.com/HowPage029.html>, retrieved Sep. 9, 2019, 2 pages.
Simo et al., "Adsorption/Desorption of Water and Ethanol on 3 A Zeolite in Near-Adiabatic Fixed Bed," Ind. Eng. Chem. Res. 48:20 (9247-9260), Sep. 2009, 14 pages.
Vaisala (online), "Vaisala HUMICAP Sensor for Measuring Moisture in Oil," Technology Description, retrieved from URL: <https://www.vaisala.com/sites/default/files/documents/HUMICAP-for-Moisture-in-oil-B211231EN-A.pdf> 2012, 2 pages.
Yang, "Chapter 2: Measurement of Oil in Produced Water," in Lee et al., Produced water, 57-88, Springer Science+Business Media, 2011, 32 pages.
PCT International Search Report and Written Opinion in International Appln. No. PCT/US2021/038365, dated Sep. 8, 2021, 13 pages.

* cited by examiner

MEASURING WATER CONTENT OF PETROLEUM FLUIDS USING DRIED PETROLEUM FLUID SOLVENT

TECHNICAL FIELD

This disclosure relates to measuring water content of hydrocarbons, for example, petroleum fluids.

BACKGROUND

Hydrocarbon produced from subsurface reservoirs through wellbores can include petroleum, water, natural gas or combinations of them. Water cut is defined as the ratio of a volume of water produced to a volume of total liquids produced through the wellbore. Water cut above a certain water cut threshold can result in inefficiencies in the processing, for example, refining, of the hydrocarbons.

SUMMARY

This disclosure describes technologies relating to measuring above-saturation water content of hydrocarbons using dried hydrocarbons as solvents.

Certain aspects of the subject matter described here can be implemented as a method. A liquid hydrocarbon sample is received from a flowline carrying the liquid hydrocarbon. The liquid hydrocarbon sample includes liquid hydrocarbon and liquid water at a concentration greater than a water saturation level. The liquid hydrocarbon sample is split into a first portion and a remainder portion. The first portion is dried to remove liquid water in the first portion. The remainder portion is mixed with the dried first portion causing the concentration of liquid water in a mixture of the remainder portion and the dried first portion to be below the water saturation level. After mixing the remainder portion with the dried first portion, a water content in the liquid hydrocarbon sample is determined.

An aspect combinable with any other aspect includes the following features. To split the liquid hydrocarbon sample into a first portion and a reminder portion, a flow control device receives the liquid hydrocarbon sample through a first fluid flow pathway. The flow control device flows the first portion into a second fluid flow pathway separate from the first. The flow control device flows the remainder portion into a third fluid flow pathway separate from the first and the second.

An aspect combinable with any other aspect includes the following features. The remainder portion is flowed through the third fluid flow pathway into a measurement cell.

An aspect combinable with any other aspect includes the following features. A temperature of the measurement cell is controlled to remain substantially at a temperature before mixing the remainder portion with the dried first portion and during determining the water content of the liquid water in the liquid hydrocarbon sample.

An aspect combinable with any other aspect includes the following features. The temperature is 40° C.

An aspect combinable with any other aspect includes the following features. To mix the remainder portion with the first dried portion, the dried first portion is flowed into the measurement cell.

An aspect combinable with any other aspect includes the following features. Before mixing the remainder portion with the dried first portion, the dried first portion is flowed from the drying chamber to a storage tank fluidically coupled to the measurement cell to flow the dried first portion from the storage tank to the measurement cell.

An aspect combinable with any other aspect includes the following features. The mixture of the remainder portion and the dried first portion is flowed from the measurement cell to the storage tank.

An aspect combinable with any other aspect includes the following features. Before mixing the remainder portion with the dried first portion, it is determined that a water content of the dried first portion is greater than a water content threshold. Responsively, an alarm signal is transmitted to cease mixing the remainder portion with the dried first portion.

An aspect combinable with any other aspect includes the following features. The water content is transmitted to a computer system. The water content is displayed on a display device connected to the computer system.

Certain aspects of the subject matter described here can be implemented as a method. At step (a), a liquid hydrocarbon sample drawn from a flowline is split into a first portion and a remainder portion. The liquid hydrocarbon sample includes liquid hydrocarbon and liquid water at a concentration greater than a water saturation level. At step (b), the first portion is dried to remove liquid water in the first portion. A quantity of the first portion is configured to reduce the liquid water to below the water saturation. At step (c), the remainder portion is mixed with the dried first portion. At step (d), after mixing the liquid hydrocarbon sample with the solvent, a water content of the liquid water in the liquid hydrocarbon sample is determined.

An aspect combinable with any other aspect includes the following features. The remainder portion is drawn into a measurement cell.

An aspect combinable with any other aspect includes the following features. To mix the remaining portion with the dried first portion, the dried first portion is flowed to a storage tank fluidically coupled to the measurement cell. The dried first portion is flowed from the storage tank into the measurement cell.

An aspect combinable with any other aspect includes the following features. Before mixing the remainder portion with the dried first portion, the dried first portion is dried to decrease water content in the dried first portion.

An aspect combinable with any other aspect includes the following features. The steps (a), (b), (c) and (d) are implemented at a first time instant and again at multiple time instants following the first time instant. Multiple water contents are determined at multiple time instants. The multiple water contents are plotted versus the multiple time instants to yield a water cut profile for the liquid hydrocarbon flowed through the flowline during the multiple time instants.

An aspect combinable with any other aspect includes the following features. The water content is transmitted to a computer system. The water content is displayed on a display device connected to the computer system.

An aspect combinable with any other aspect includes the following features. The mixture of the solvent and the liquid hydrocarbon sample is flowed into the flowline.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Certain crude oil processing refineries specify that the maximum water content of exported crude oil should be less than a water content threshold, for example, 0.2 weight percentage (wt. %). Water content at or below such threshold reduces processing cost for the refineries as well as the handling of contaminated water. If the water concentration in the liquid hydrocarbon is below water saturation level, then capacitance probes can be used to measure water content on the basis that the water concentration is homogeneous. However, if the water concentration is above saturation, then the assumption is invalid and the capacitance-based measurement techniques may be inaccurate. This disclosure describes adding a known amount of liquid hydrocarbon sample that includes liquid hydrocarbons and liquid water to a known amount of a solvent, for example, a low-dielectric solvent, such as dry xylene. In the context of this disclosure, a low-dielectric solvent is one that has a dielectric constant of less than five. More generally, a low-dielectric solvent is one that offers good compatibility with crude oil facilitating mixing and having low affinity with water to avoid large water uptake during storage that would be difficult to remove with a molecular sieve. The quantity of the solvent and the sample is chosen such that the water concentration in the sample will be below the water saturation level. The water cut in the mixture can then be measured, for example, using the capacitance-based measurement technique describes earlier. In the context of this disclosure, water saturation refers to a saturation point, that is, the threshold value, of water concentration above which water cannot be dissolved in the solvent anymore, and will be found in dispersed form of droplets or as a sediment within the solvent.

The online water cut measurement system described here can provide the ability to control the product streams closer to a refinery's specifications, for example, adjusting demulsifier and wash water flow rates. The techniques described here can be implemented for continuous, real-time water content measurements that can alert operators on changes in the water content of liquid hydrocarbons carried in flowlines. Such alerts can also enable the operators to change the process operation or to alert other operators of potential malfunction in upstream equipment. The water cut measurement techniques described here can provide accurate water cut data in an entire range of water concentration, that is, 0% to 100% range, more specifically, the 0% to 1% range. In addition, the techniques described here enable water cut measurement in liquid hydrocarbons with liquid water above water saturation levels.

Figure 1:
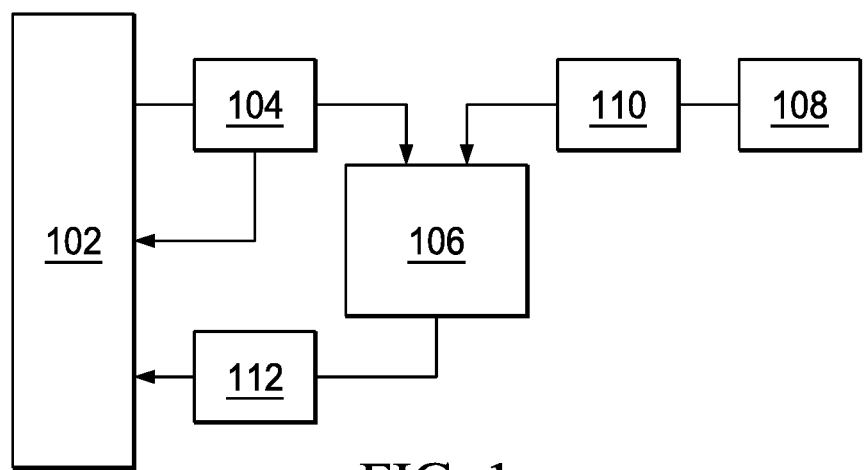
FIG. 1 is a schematic of an implementation of a system for measuring water cut in a liquid hydrocarbon sample.

FIG. 1 is a schematic of an implementation of a system for measuring water cut in a liquid hydrocarbon sample. The system includes a flowline 102 carrying liquid hydrocarbons. In some implementations, the flowline 102 can carry the liquid hydrocarbons produced through a wellbore (not shown). For example, the flowline 102 can run from a wellhead to a different location, for example, a gas oil separation plant (GOSP) or from a GOSP to a crude oil export terminal or stabilization plant. The liquid hydrocarbons flowed in the flowline 102 can include liquid water and, for example, liquid crude oil. A fast loop system 104 is fluidically coupled to the flowline 102 to obtain a liquid hydrocarbon sample from the flowline 102. The fast loop system 104 can be any fluidic system that includes an inlet and an outlet (for example, a drain) and that is fluidically coupled to a main line (here, the flowline 102). The fast loop system 104 can establish a continuous flow of fresh liquid hydrocarbon sample for the analysis described later. The fast loop system 104 can be configured to draw a desired quantity of the liquid hydrocarbon sample and a desired frequency at which the sample is to be drawn, for example, using a solenoid valve or an equivalent mechanism. In some implementations, the fast loop system 104 can be equipped with a flow metering system, a pump to allow reinjection into the flowline 102, or a filtering system (or a combination of any two or all three of them).

A measurement cell 106 is fluidically coupled to the fast loop system 104. A volume of a liquid hydrocarbon sample drawn from the flowline 102 by the fast loop system 104 is flowed to the measurement cell 106. The volume of the measurement cell 106 is determined by the volume of the liquid hydrocarbon sample used to measure the water cut. Excessively low volumes can lead to inaccuracies in measurement whereas excessively high volumes can increase the implementation cost. In some examples, the volume of the liquid hydrocarbon sample can be 10 milliliters (ml). In some implementations, the fast loop system 104 can include a flow pathway that returns the sample to the flowline 102 before the sample is flowed to the measurement cell 106. The fast loop system 104 allows conditioning the hydrocarbon sampled from the flowline 102, for example, in terms of pressure, flow rate and filtration requirements, and providing a fresh sample to the measurement cell 106. In some implementations, the fast loop system 104 can provide the fresh sample at a frequency that matches the required measurement frequency, thereby avoiding product loss. Product not used for measurement is returned to the flowline 102.

The liquid hydrocarbon sample drawn into the measurement cell 106 includes liquid water at a concentration greater than the water saturation level. The concentration of the liquid water is decreased by adding a solvent, for example, a dielectric solvent such as xylene. In general, water and oil do not mix. However, dielectric solvents, such as xylene, can solubilize a minimal amount of water. Table 1 lists water solubility of certain solvents at a reference temperature. For example, xylene has a water solubility of 391 parts per million (ppm) at 25 centigrade (° C.). This means that each liter of dry xylene can solubilize up to 391 microliters (μl) of water. As water exceeds this concentration, it will drop out of the solution in the form of droplets and eventually form a sedimentation layer. In this disclosure the solvent to crude oil ratio is determined to meet the condition of solubility in the range of measurement of interest.

TABLE 1

BS&W stands for basic sediment and water and is a measure of free water, sediment and emulsion measured as a volume percentage of a production stream.

| Solvent | Water solubility @25° C. | | Max BS&W in crude oil vs crude-solvent ratio (volume) | | | | | | |
|---|---|---|---|---|---|---|---|---|---|
| | mol/l | Ppm | 1 to 1 | 1 to 10 | 1 to 20 | 1 to 30 | 1 to 40 | 1 to 50 | 1 to 100 |
| Hexadecane | 0.0029 | 52 | 0.005% | 0.052% | 0.104% | 0.157% | 0.209% | 0.261% | 0.522% |
| Cyclohexane | 0.003 | 54 | 0.005% | 0.054% | 0.108% | 0.162% | 0.216% | 0.270% | 0.540% |
| CCl4 | 0.0087 | 157 | 0.016% | 0.157% | 0.313% | 0.470% | 0.627% | 0.784% | 1.567% |
| p-Xylene | 0.0217 | 391 | 0.039% | 0.391% | 0.782% | 1.173% | 1.564% | 1.955% | 3.909% |
| Toluene | 0.0265 | 477 | 0.048% | 0.477% | 0.955% | 1.432% | 1.910% | 2.387% | 4.774% |
| Benzene | 0.0349 | 629 | 0.063% | 0.629% | 1.257% | 1.886% | 2.515% | 3.144% | 6.287% |
| Chlorobenzene | 0.029 | 522 | 0.052% | 0.522% | 1.045% | 1.567% | 2.090% | 2.612% | 5.224% |
| o-Dichlorobenzene | 0.024 | 432 | 0.043% | 0.432% | 0.865% | 1.297% | 1.729% | 2.162% | 4.324% |
| Chloroform | 0.0732 | 1319 | 0.132% | 1.319% | 2.637% | 3.956% | 5.275% | 6.593% | 13.19% |
| 1,2-Dichloroethane | 0.1262 | 2273 | 0.227% | 2.273% | 4.547% | 6.820% | 9.094% | 11.37% | 22.73% |
| 1,1,2,2-Tetrachloroethane | 0.101 | 1820 | 0.182% | 1.820% | 3.639% | 5.459% | 7.278% | 9.098% | 18.20% |

At higher temperatures than that reported in Table 1, it is expected that the solubility values will be larger, thereby extending the range of measurable water content. In one study, the solubility of water in p-xylene versus temperature at 689.5 kiloPascal (kPa) was measured. It was found that, for each incremental degree of temperature, the solubility increased by approximately 0.7% between 25° C. and 100° C. Therefore, a measurement at 60° C. rather than 25° C. would extend the water measurement range by 30%.

In some implementations, the solvent is stored in a solvent storage tank 108 that is fluidically coupled to the measurement cell 106. Depending on the application, the solvent in the solvent storage tank 108 can be xylene or another low dielectric solvent mentioned in Table 1. The solvent in the solvent storage tank 108 is in a liquid state. The solvent can be flowed from the solvent storage tank 108 to the measurement cell 106 using a pump (not shown). Alternatively, a pressure variation between the measurement cell 106 and the solvent storage tank 108 can be used to draw the solvent from the solvent storage tank 108 into the measurement cell 106. For example, pressure variation can be created by pressurizing the solvent storage tank 108 with a dry gas (for example, nitrogen from a gas cylinder or dry instrument air from the plant). In this manner, a determined, for example, metered, quantity of the solvent can be flowed from the solvent storage tank 108 to the measurement cell 106.

The quantity of the solvent drawn into the measurement cell 106 can be selected based on the volume of the liquid hydrocarbon sample drawn into the measurement cell 106 as well as the expected water cut measured by BS&W. For example, as shown in Table 1, to measure up to 0.782% water in a wet crude oil/xylene system, the crude oil/xylene ratio should be 1:20. For a measurement cell having a volume of 10.5 ml, this translates to 0.5 ml of crude oil and 10 ml of xylene, approximately.

In some implementations, the solvent storage tank 108 and the measurement cell 106 are directly fluidically coupled, that is, through a pipeline and without any intermediate element. In general, the low dielectric solvent in the solvent storage tank 108 is substantially water-free or, at minimum, has a water content below a water content threshold. In some implementations, the water content of the solvent can be further lowered by flowing the solvent through a drying chamber 110 prior to flowing the solvent to the measurement cell 106. For example, the drying chamber 110 can be fluidically coupled to the measurement cell 106 on one end and to the solvent storage tank 108 on another end. The solvent can be flowed from the solvent storage tank 108 to the drying chamber 110. Drying can be implemented using silica gel, activated alumina, zeolites, or a combination of them. For example, the drying chamber 110 can include or can be implemented as crystalline metal aluminosilicates having a three-dimensional interconnecting network of silica and alumina tetrahedra. Such implementations are effective to remove water from organic liquids.

In some implementations, the drying chamber 110 need not be a separate container in which the drying agents are disposed. Rather, the drying chamber 110 can be implemented as three Angstrom (3 A) to 5 A type molecular sieves disposed within the flow pathway, that is, the tubes or pipes, through which the solvent is flowed from the solvent storage tank 108 to the measurement cell 106. Such molecular sieves can remove water from xylenes, since water molecules have 1.93 A size while xylenes have molecular size in the 6.5 A to 7.5 A range.

In some implementations, dry gas (for example, dry nitrogen or similar inert gas) is injected into the measurement cell 106 with the solvent. To create an overpressure and avoid moisture contamination in the solvent. Doing so can reduce the load on the drying agents and improve the dehydration process efficiency. In some implementations, a cartridge containing a molecular sieve or other drying agent can be located at an inlet of the solvent storage tank 108 to avoid water entering the tank. In such implementations, the drying chamber 110 can function as a second cartridge to ensure complete dryness of the solvent before the solvent enters the measurement cell 106. Both, the cartridge at the inlet of the solvent storage tank 108 and the drying chamber 110, can be replaced periodically to ensure that water is collected efficiently. Certain types of cartridges (or the drying chamber) can be regenerated by heating above 120° C. under inert sweep to displace water from the molecular sieve.

After a quantity of the liquid hydrocarbon sample drawn from the flowline 102 and a quantity of the solvent drawn from the solvent storage tank 108 are flowed to the measurement cell 106, the water cut of the mixture is measured. In some implementations, dry inert gas can be bubbled into the measurement cell 106 to facilitate mixing between the solvent and the sample. To do so, the measurement cell 106 is maintained at a particular temperature, for example, 40° C. In some implementations, the measurement cell 106 can be connected to a heater (not shown) or be positioned within a heating chamber (not shown) to maintain the measurement cell 106 at the particular temperature.

With the temperature of the measurement cell 106 maintained at the desired temperature, a water cut of the mixture within the measurement cell 106 is measured. The water cut can be measured by a capacitance type meter.

In some implementations, the measurement cell 106 is operatively coupled to a computer system (not shown). The computer system includes a computer-readable medium (for example, transitory or non-transitory computer-readable medium) storing instructions executable by one or more processors to perform operations. The operations include receiving water cut measurements from the measurement cell 106. For example, a sensor is installed inside the measurement cell 106 and can measure the water cut. The sensor is operatively coupled to the computer system and can transmit the water cut to the computer system. The computer system is operatively coupled to a display device (not shown). The computer system can display the water cut of a sample or generate and display a water cut profile (described later) of multiple samples in the display device. In some implementations, the water cut (or BS&W) can be displayed on the electronic enclosure of the water cut analyzer itself or sent remotely to a plant control room through a plant information (PI) system or similar data transmission system.

After the water cut of the sample has been measured, the sample is recovered from the measurement cell 106 and returned to the flowline 102. In some implementations, a sample recovery system 112 is fluidically coupled to the measurement cell 106 on one end and the flowline 102 on another end. In some implementations, the sample recovery system 112 includes a tank receiving the solvent-hydrocarbon mixture from the measurement cell 106. The sample recovery system 112 can be connected to a pump and emptied periodically either to a drain or into the flowline 102.

Figure 2:
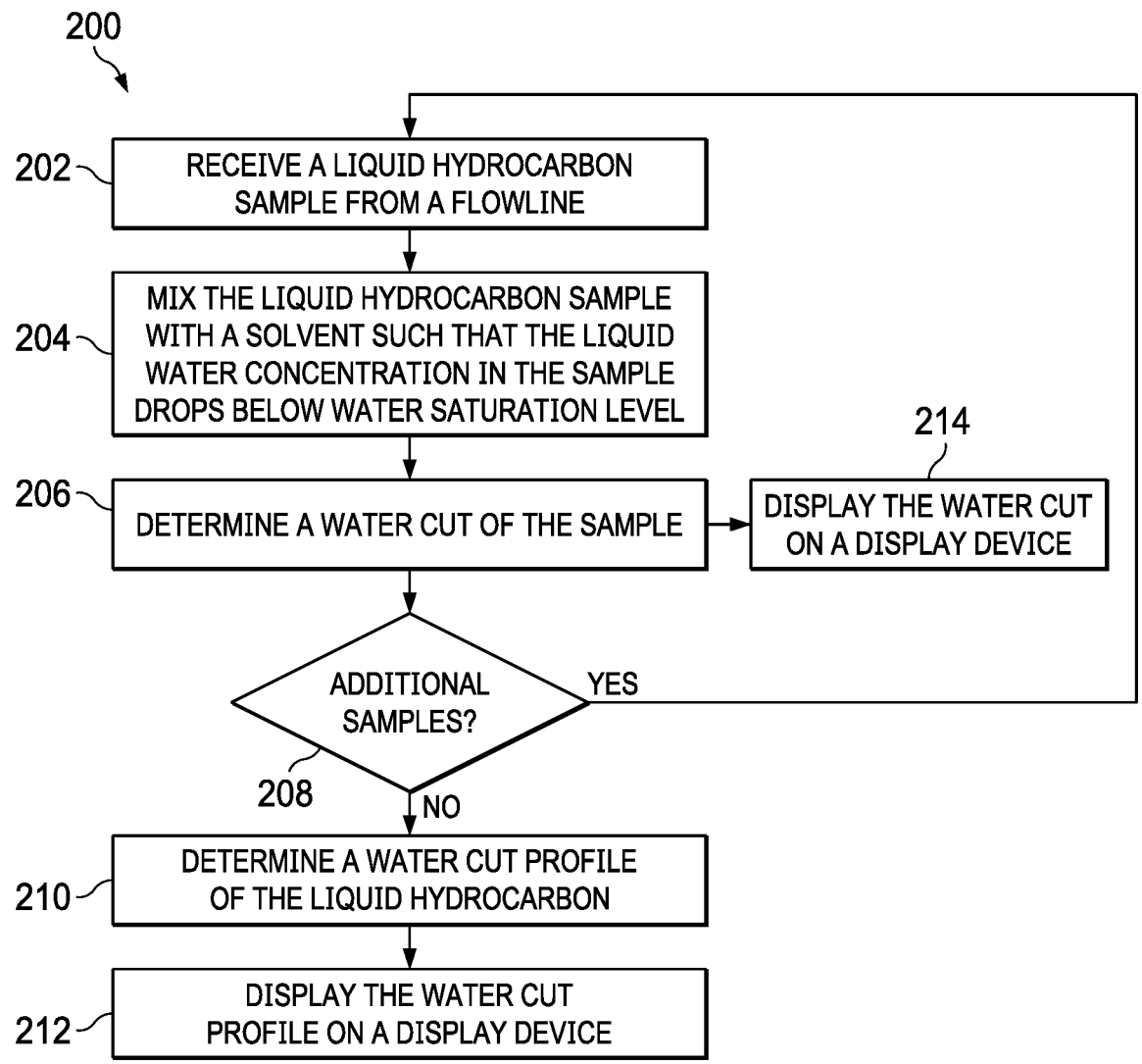
FIG. 2 is a flowchart of an example of a process for measuring water cut in a liquid hydrocarbon sample.

FIG. 2 is a flowchart of an example of a process 200 for measuring water cut in a liquid hydrocarbon sample. At 202, a liquid hydrocarbon sample is received from a flowline, for example, the flowline 102. At 204, the liquid hydrocarbon sample is mixed with a solvent, for example, from the solvent stored in the solvent storage tank 108. The mixing is implemented, for example, in the measurement cell 106. At 206, a water cut of the sample is determined. At 214, the water cut is displayed, for example, on the display device of a computer system. At 208, it is determined if additional samples are to be measured for water content. If additional samples are to be measured (decision branch "YES"), then steps 202, 204 and 206 are repeated to determine the water cuts for multiple respective samples. In particular, each additional sample is drawn from the flowline at a respective time instant, and its water cut is measured. The frequency at which the different samples are drawn and water cut measured can depend upon the operation being performed or the process being controlled. For example, four samples can be drawn and measured periodically, that is, at equal time intervals, each hour. In this manner, water cuts of multiple samples drawn from the flowline over a duration that spans multiple time instants is obtained. If no additional samples remain (decision branch "NO"), then, at 210, a water cut profile of the liquid hydrocarbon is determined. The water cut profile is a plot of water cuts of the multiple samples versus the respective time instants at which the multiple samples were drawn from the flowline 102 or at which the water cut was measured for the multiple samples. The computer system can generate the water cut profile using any plot or graph generation software. At 214, the water cut is displayed on the display device.

In the implementation described with reference to FIGS. 1 and 2, the liquid hydrocarbon sample was drawn from the flowline 102 at a particular height measured from the bottom of the flowline 102. In such an implementation, the water cut of each sample or the water cut profile of multiple samples is representative of the water cut in the liquid hydrocarbon flowing through the flowline 102 at the measured height. In some implementations, the techniques described here can be implemented to determine water cut at different heights in a separation vessel. Recognizing that the water cut can be different at different heights within the vessel, multiple samples can be drawn from the vessel at different heights measured from the bottom of the vessel. By doing so, a water cut profile across a height of the vessel can be determined. Using the water cut or water cut profile (or both) measured as described in this disclosure, a control system can be programmed to create a relationship between water cut, that is, BS&W readings, and certain operations, for example, wash water flow rate, demulsifier flow rate, opening of recirculation valve, heating requirements in the presence of a heat exchanger or similar wellbore, flowline or plant operations. Off-spec crude oil can be segregated and sent to different tanks. In some implementations, a mixing element, for example, a static mixer, can be disposed in the flowline 102 and the hydrocarbon can be sampled downstream of the mixing element to ensure mixing of the hydrocarbons and obtaining a representative sample.

Example

Figure 3:
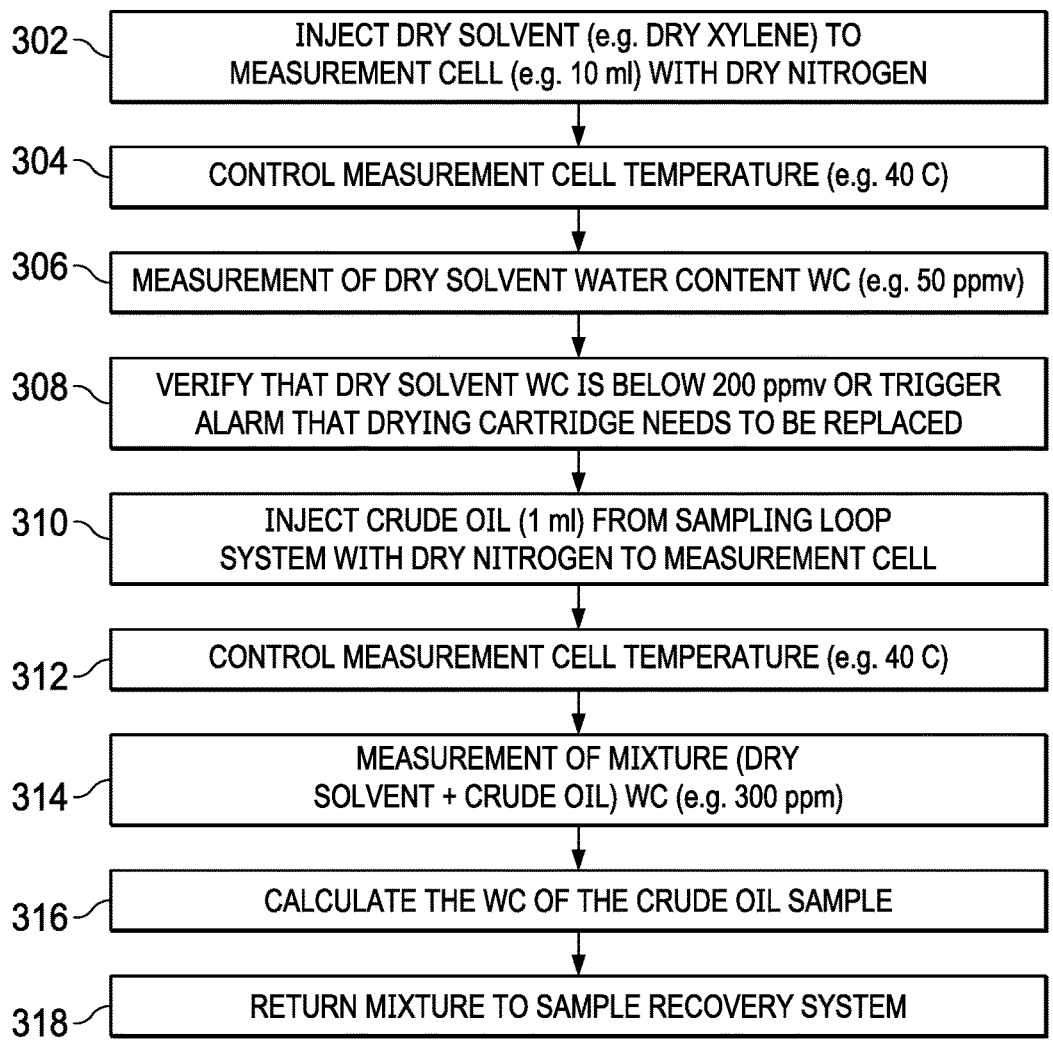
FIG. 3 is a description of an example of a process for measuring water cut in a liquid hydrocarbon sample.

FIG. 3 is a description of an example of a process for measuring water cut in a liquid hydrocarbon sample. At 302, dry xylene was injected into a 10 ml measurement cell with dry nitrogen. At 304, the temperature of the measurement cell was controlled at 40° C. At 306, water content in dry solvent was measured. The water content was found to be 50 parts per million by volume (ppmv). At 308, it was verified that the dry solvent water content was below a water content threshold of 200 ppmv. If the dry solvent water content had been greater than the water content threshold, then an alarm would have triggered requiring replacement of the solvent or the molecular sieve cartridge at the inlet of the solvent storage tank. At 310, 1 ml of crude oil was injected from the fast loop system with dry nitrogen into the measurement cell. At 312, a temperature of the measurement cell was maintained at 40° C. At 314, water content of the mixture of dry solvent and liquid hydrocarbon sample in the measurement cell was measured to be 300 ppm. At 316, the water cut of the liquid hydrocarbon sample was determined. In particular, the water cut of the crude oil sample was measured using the following formula:

$$\text{Liquid } HC\ WC = \frac{(mix.\ vol. \times mix.\ WC) - (\text{dry solvent } vol. \times \text{dry solvent } WC)}{\text{Liquid } HC \text{ volume}}$$

In the formula above, "mix. vol." stands for the volume of the mixture of the liquid hydrocarbon (HC) sample and the solvent and "mix. WC" stands for the water cut of the mixture. In this example, the liquid HC WC was 2800 ppm or 0.28%. At 318, the mixture was returned to the flowline through the sample recovery system.

In some implementations, the water cut measurement system described here can be calibrated. To do so, two samples can be drawn, either simultaneously or at different time instants. The samples can be diluted differently. For example, the first sample can be diluted at a 1:10 ratio, and the second sample can be diluted at a 1:20 ratio with a dilusion fluid, for example, the low-dielectric solvent. The water cut measurement can be implemented for both samples are described earlier. If the system operates as intended, then the water cut of the first sample will be twice that of the second sample. When similar calibration is implemented for multiple samples with a linear range of dilution ratios, the water cut profile for the samples will also be linear. Alternatively or in addition, processing two water samples of the same concentration (1:10 ratio or 1:20 ratio) in parallel allows solving a system of two equations with two unknowns (the original water contents in the hydrocarbons and the solvent), enabling measurement of the water content of the mixture components.

Figure 4:
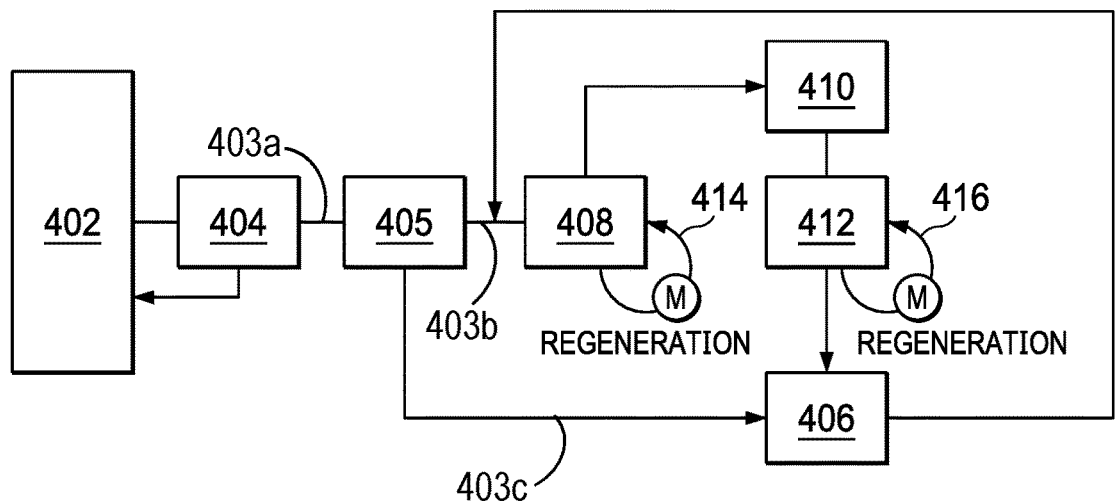
FIG. 4 is a schematic of another implementation of a system for measuring water cut in a liquid hydrocarbon sample.

FIG. 4 is a schematic of another implementation of a system for measuring water cut in a liquid hydrocarbon sample. In the system described with reference to FIG. 1, the concentration of water in the hydrocarbon sample was decreased by adding a quantity of a dry solvent to the sample. In contrast, in the system described with reference to FIG. 4, a quantity of the hydrocarbon sample itself is first dried and then added to the undried hydrocarbon sample such that the dried hydrocarbon sample reduces the concentration of water in the undried hydrocarbon sample. Although the systems described in this disclosure have been described in the context of evaluating a liquid hydrocarbon sample, the systems can also be used to similarly evaluate other liquids such as engine lubricants, turbine oils, crankcase oil, transformer oil, hydraulic oils, heavy oils, bio-gasoline and cutting oils.

The system includes a flowline 402 substantially similar to flowline 102. Like the flowline 102, the flowline 402 can also carry the liquid hydrocarbons produced through a wellbore (not shown). For example, the flowline 402 can run from a wellhead to a different location, for example, a gas oil separation plant (GOSP) or from a GOSP to a crude oil export terminal or stabilization plant. The liquid hydrocarbons flowed in the flowline 402 can include liquid water and, for example, liquid crude oil. A fast loop system 404, substantially similar to the fast loop system 104, is fluidically coupled to the flowline 402 to obtain a liquid hydrocarbon sample from the flowline 402. The fast loop system 404 can be configured to draw a desired quantity of the liquid hydrocarbon sample and a desired frequency at which the sample is to be drawn, for example, using a solenoid valve or an equivalent mechanism. In some implementations, the fast loop system 404 can be equipped with a flow metering system, a pump to allow reinjection into the flowline 402, or a filtering system (or a combination of any two or all three of them).

In some implementations, the liquid hydrocarbon sample drawn by the fast loop system 404 is flowed through a fluid flow pathway 403a and split into two branches, for example, by a flow control device 405 (for example, a 3-way splitter or a T-splitter) operable with or without valves. As described later, one branch of the liquid hydrocarbon sample is flowed through a fluid flow pathway 403b, dried and used as a solvent to decrease the concentration of water in the other branch of the liquid hydrocarbon sample. The quantity of the liquid hydrocarbon sample flowed into one branch to be subsequently dried depends on the quantity of the liquid hydrocarbon sample flowed into the other branch to be tested. Therefore, the flow control device 405 can include a controllable flow meter (not shown) that can meter the quantity of the liquid hydrocarbon sample needed for drying and accordingly split the liquid hydrocarbon sample. In some implementations, the fast loop system 404 can include a flow pathway that returns the sample to the flowline 402 before the sample is flowed to the flow control device 405. The fast loop system 404 allows conditioning the hydrocarbon sampled from the flowline 402, for example, in terms of pressure, flow rate, and filtration requirements, and providing fresh sample to the flow control device 405. In some implementations, the fast loop system 404 can provide the fresh sample at a frequency that matches the required measurement frequency, thereby avoiding product loss. Product not used for measurement is returned to the flowline 402.

A measurement cell 406 (substantially similar to the measurement cell 106) is fluidically coupled to the flow control device 405. A quantity of the liquid hydrocarbon sample drawn from the flowline 402 by the fast loop system 404 and split by the flow control device 405 is flowed to the measurement cell 406 through a fluid flow pathway 403c. The volume of the measurement cell 406 is determined by the quantity of the liquid hydrocarbon sample used to measure the water cut. Excessively low volumes can lead to inaccuracies in measurement whereas excessively high volumes can increase the implementation cost. In some examples, the volume of the liquid hydrocarbon sample can be 10 milliliters (ml).

The liquid hydrocarbon sample drawn into the measurement cell 406 can have liquid water at a concentration greater than the water saturation level. Before testing the water level in the sample, the concentration needs to be reduced to below the water saturation level. To do so, the branch of the liquid hydrocarbon sample not flowed to the measurement cell 406 is dried. In particular, that branch of the liquid hydrocarbon sample is flowed through a drying chamber 408 (substantially similar to the drying chamber 110). For example, the drying chamber 408 can be fluidically coupled to flow control device 405 on one end and to a storage tank 410 storage tank 410 (substantially similar to the solvent storage tank 108) on another end. The branch of the liquid hydrocarbon sample from the flow control device 405 through the drying chamber 408 and the dried liquid hydrocarbon sample can be flowed to the storage tank 410. Drying in the drying chamber 408 can be implemented using silica gel, activated alumina, zeolites or a combination of them. For example, the drying chamber 408 can include or can be implemented as crystalline metal aluminosilicates having a three-dimensional interconnecting network of silica and alumina tetrahedra. Such implementations are effective to remove water from organic liquids.

In some implementations, the drying chamber 408 need not be a separate container in which the drying agents are disposed. Rather, the drying chamber 408 can be implemented as three Angstrom (3 A) to 5 A type molecular sieves disposed within the flow pathway, that is, the tubes or pipes, through which the liquid hydrocarbon sample is flowed from the flow control device 405 to the storage tank 410. Such molecular sieves can remove water from the liquid hydrocarbon sample, since water molecules have size below 3 A while typical hydrocarbons' molecular size falls in a higher size range than the sieves' pores. For example, ethylene, propane and toluene have size of 4.2 A, 4.9 A and 6.7 A, respectively. Selection of the most appropriate molecular sieve will depend on the particular application.

The dried liquid hydrocarbon sample can be flowed from the storage tank 410 to the measurement cell 406 using a pump (not shown). Alternatively, a pressure variation between the measurement cell 406 and the storage tank 410 can be used to draw the dried liquid hydrocarbon sample from the storage tank 410 into the measurement cell 406. For example, pressure variation can be created by pressurizing the storage tank 410 with a dry gas (for example, nitrogen from a gas cylinder or dry instrument air from the plant). In this manner, a determined, for example, metered, quantity of the solvent can be flowed from the storage tank 410 to the measurement cell 406.

In some implementations, all of the dried liquid hydrocarbon sample can be flowed to the measurement cell 406 to be mixed with the undried liquid hydrocarbon sample. In such implementations, as described earlier, the quantity of the liquid hydrocarbon sample to be dried is chosen based on the volume of the measurement cell 406 and its capacity to hold undried liquid hydrocarbon sample. In some implementations, the storage tank 410 can be filled with more dried liquid hydrocarbon sample than needed for each instance of measuring the water cut. That is, over time, more liquid hydrocarbon sample than needed for each instance of measuring the water cut in the measurement cell 406 has been flowed to the storage tank 410 after being dried in the drying chamber 408, and dried liquid hydrocarbon sample has accumulated in the storage tank 410. In such implementations, to measure water cut in a new liquid hydrocarbon sample, the flow control device 405 need not split the liquid hydrocarbon sample into two branches—one for drying and the other for testing—because dried liquid hydrocarbon sample is already available in the storage tank 410. Consequently, the quantity of liquid hydrocarbon sample drawn by the fast loop system 404 can be decreased and the flow control device 405 can route all of the drawn liquid hydrocarbon sample to the measurement cell 406. Conversely, in some implementations, upon determining that the quantity of dried liquid hydrocarbon sample in the storage tank 410 is less than a threshold quantity (for example, the storage tank 410 is empty), liquid hydrocarbon sample drawn from the flowline 402 by the fast loop system 404 can be flowed in its entirety to the drying chamber 408 and then to the storage tank 410. In such instances, none of the drawn liquid hydrocarbon sample is flowed to the measurement cell 406 because the goal is not to measure water cut, but rather to accumulate dried liquid hydrocarbon sample over time. In sum, depending on the quantity of dried liquid hydrocarbon sample stored in the storage tank 410, the fast loop system 404 can be configured to vary a quantity of the liquid hydrocarbon sample drawn from the flowline 402, and the flow control device 405 can be configured to either split the drawn liquid hydrocarbon sample into two branches or to flow all of the liquid hydrocarbon sample to either the drying chamber 408 or the measurement cell 406.

The quantity of the dried liquid hydrocarbon sample drawn into the measurement cell 406 can be selected based on the volume of the liquid hydrocarbon sample drawn into the measurement cell 406 as well as the expected water cut measured by BS&W. For example, as shown in Table 1, to measure up to 0.16% water in a Gasoline 12 system, the undried/dried liquid hydrocarbon sample ratio should be 1:20. For a measurement cell having a volume of 10.5 ml, this translates to 0.5 ml of undried liquid hydrocarbon sample and 10 ml of dried liquid hydrocarbon sample, approximately.

In some implementations, the storage tank 410 and the measurement cell 406 are directly fluidically coupled, that is, through a pipeline and without any intermediate element. In general, the dried liquid hydrocarbon sample in the storage tank 410 is substantially water-free or, at minimum, has a water content below a water content threshold. In some implementations, the water content of the dried liquid hydrocarbon sample can be further lowered by flowing the dried liquid hydrocarbon sample through another drying chamber 412. The drying chamber 412 can be implemented in case the storage tank 410 is pressurized with gas to establish flow into the regeneration system 416. The drying chamber 412 can remove moisture that may have contaminated the gas or in case moisture is introduced into the process when replacing a gas cylinder or performing other maintenance operations. Each of the drying chambers 408 and 412 can include a respective regeneration system 414 and 416. Each regeneration system 414, 416 includes a heater that can heat the respective drying chamber, thereby drying the drying chamber so that it can maintain its drying capacity without needing a full replacement upon becoming saturated. The heater can be heated to or above 120° C. under inert sweep to displace water from the molecular sieve in the drying chamber. Higher regeneration temperatures of 175° C. to 315° C. can be employed for other types of sieves (for example, type 3 A, 4 A, 5 A). Sweep gas resulting from the regeneration can be routed to a flare recovery system, a thermal oxidizer or otherwise safely vented to atmosphere depending on plant and local legislation for emissions.

The concentration of the liquid water in the undried liquid hydrocarbon sample is decreased by adding the dried liquid hydrocarbon sample. In general, water and oil do not mix. However, the dried liquid hydrocarbon sample can solubilize a minimal amount of water. Table 2 lists water solubility of certain petroleum fractions at a reference temperature. For example, Gasoline 10 has a water solubility of 193 parts per million (ppm) at 50 centigrade (° C.). This means that each liter of dry Gasoline 10 can solubilize up to 193 microliters (μl) of water. As water exceeds this concentration, it will drop out of the solution in the form of droplets and eventually form a sedimentation layer. In this disclosure the dry liquid hydrocarbon sample to undried liquid hydrocarbon sample ratio is determined to meet the condition of solubility in the range of measurement of interest.

TABLE 2

BS&W stands for basic sediment and water and is a measure of free water, sediment and emulsion measured as a volume percentage of a production stream.

| Petroleum fraction | Boiling point [° C.] | Temperature [° C.] | Solubility of water at ref. temperature [ppm] | Max detectable BS&W vs wet/dry fraction ratio | | | | | |
|---|---|---|---|---|---|---|---|---|---|
| | | | | 1 to 10 | 1 to 20 | 1 to 30 | 1 to 50 | 1 to 100 | 1 to 500 |
| Gasoline 10 | 58.9 | 50 | 193 | 0.21% | 0.41% | 0.60% | 0.99% | 1.95% | 9.68% |
| Gasoline 12 | 80.6 | 50 | 74 | 0.08% | 0.16% | 0.23% | 0.38% | 0.75% | 3.70% |
| Gasoline 13 | 86.1 | 50 | 111 | 0.12% | 0.23% | 0.34% | 0.57% | 1.12% | 5.56% |
| Gasoline 15 | 93.9 | 50 | 207 | 0.23% | 0.44% | 0.64% | 1.06% | 2.09% | 10.38% |
| Gasoline 19 | 62.8 | 50 | 64 | 0.07% | 0.13% | 0.20% | 0.32% | 0.64% | 3.18% |
| Naphtha | 172.2 | 159 | 6086 | 6.69% | 12.78% | 18.87% | 31.04% | 61.47% | 100.00% |
| Kerosene | 226.1 | 112 | 1226 | 1.35% | 2.58% | 3.80% | 6.25% | 12.39% | 61.44% |
| Lubricating oil | 445.0 | 124 | 1067 | 1.17% | 2.24% | 3.31% | 5.44% | 10.78% | 53.47% |

At higher temperatures than that reported in Table 1, it is expected that the solubility values will be larger, thereby extending the range of measurable water content.

In some implementations, dry gas (for example, dry nitrogen or similar inert gas) is injected into the measurement cell 406 with the dried liquid hydrocarbon sample to create an overpressure and avoid moisture contamination in the dried liquid hydrocarbon sample. Doing so can reduce the load on the dried liquid hydrocarbon sample and improve the dehydration process efficiency. In some implementations, a cartridge containing a molecular sieve or other drying agent can be located at an inlet of the storage tank 410 to avoid water entering the tank. In such implementations, the drying chamber 408 can function as a second cartridge to ensure complete dryness of the dried liquid hydrocarbon sample before that sample enters the measurement cell 406. Both the cartridge at the inlet of the storage tank 410 and the drying chamber 408 can be replaced periodically to ensure that water is collected efficiently.

After a quantity of the undried liquid hydrocarbon sample drawn from the flowline 402 and a quantity of the dried liquid hydrocarbon sample drawn from the storage tank 410 are flowed to the measurement cell 406, the water cut of the mixture is measured. In some implementations, dry inert gas can be bubbled into the measurement cell 406 to facilitate mixing between the dried and undried samples. To do so, the measurement cell 406 is maintained at a particular temperature, for example, 40° C. In some implementations, the measurement cell 406 can be connected to a heater (not shown) or be positioned within a heating chamber (not shown) to maintain the measurement cell 406 at the particular temperature.

With the temperature of the measurement cell 406 maintained at the desired temperature, a water cut of the mixture within the measurement cell 106 is measured. The water cut can be measured by a capacitance or fiber optic type meter, by Karl Fischer, or by NIR spectroscopy.

In some implementations, the measurement cell 406 is operatively coupled to a computer system (not shown). The computer system includes a computer-readable medium (for example, transitory or non-transitory computer-readable medium) storing instructions executable by one or more processors to perform operations. The operations include receiving water cut measurements from the measurement cell 406. For example, a sensor is installed inside the measurement cell 406 and can measure the water cut. The sensor is operatively coupled to the computer system and can transmit the water cut to the computer system. The computer system is operatively coupled to a display device (not shown). The computer system can display the water cut of a sample or generate and display a water cut profile (described later) of multiple samples in the display device. In some implementations, the water cut (or BS&W) can be displayed on the electronic enclosure of the water cut analyzer itself or sent remotely to a plant control room through a plant information (PI) system or similar data transmission system.

In some implementations, after the water cut of the sample has been measured, the sample is recovered from the measurement cell 406 and returned to the flowline 402. Alternatively, the sample from the measurement cell 406 can be flowed to the drying chamber 408 to be prepared as dried liquid hydrocarbon sample for subsequent water cut measurements and then to be stored in the storage tank 410. In such implementations, the quantity of the dried liquid hydrocarbon in the storage tank 410 can be stored. If the quantity exceeds a threshold, then the mixture of the dried and undried liquid hydrocarbon sample can be flowed from the measurement cell 406 back to the flowline 402 after the water cut measurement. Flow of the sample from the measurement cell 406 to either the drying chamber 408 or the flowline 402 can be implemented by a pump (not shown) fluidically coupled to the measurement cell 406.

Figure 5:
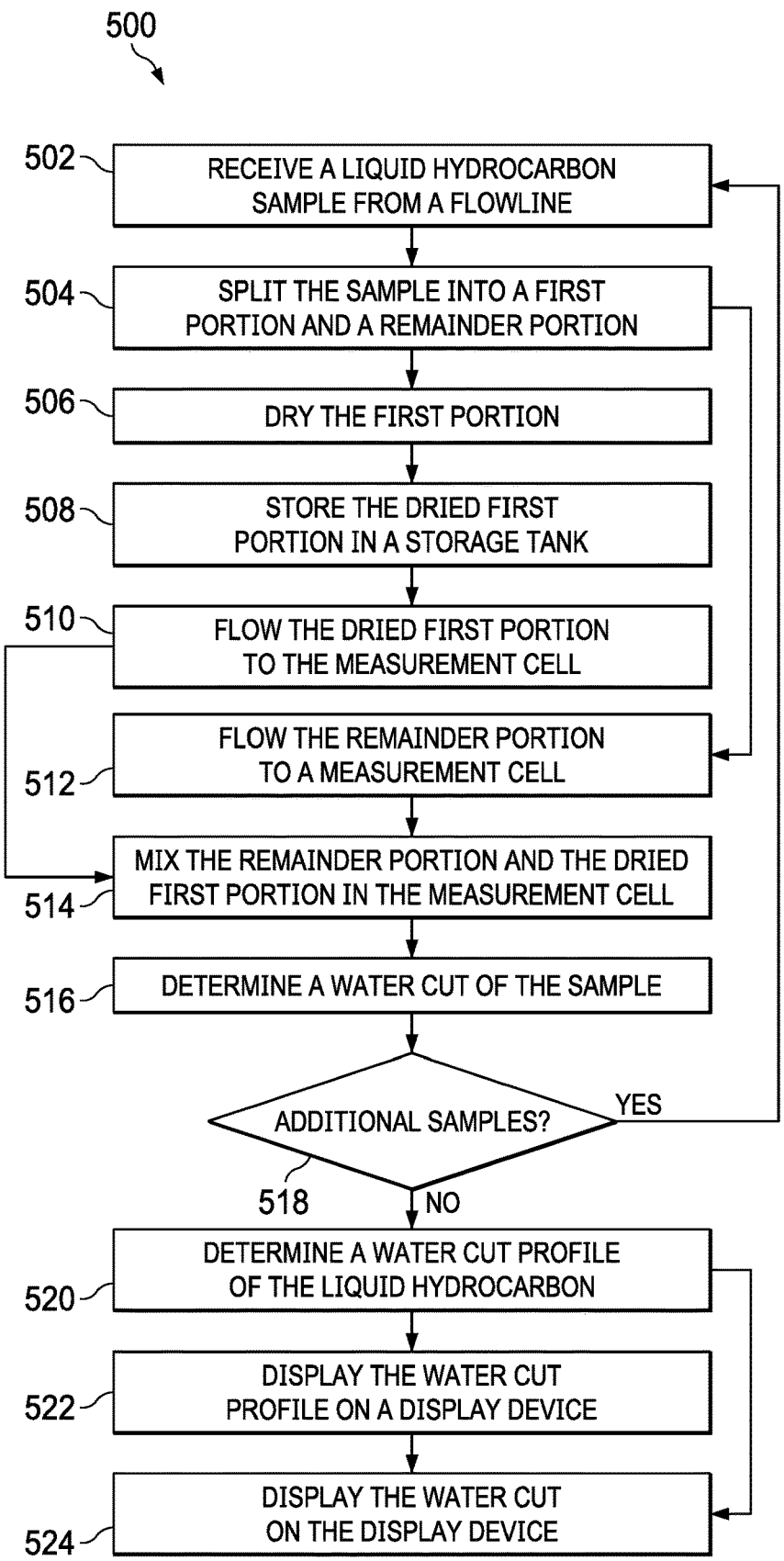
FIG. 5 is a flowchart of an example of another process for measuring water cut in a liquid hydrocarbon sample.

FIG. 5 is a flowchart of an example of another process 500 for measuring water cut in a liquid hydrocarbon sample. At 502, a liquid hydrocarbon sample is received from a flowline, for example, the flowline 402. At 504, the liquid hydrocarbon sample is split into a first portion and a remainder portion. For example, the flow control device 405 splits the liquid hydrocarbon sample into the first portion and the remainder portion. The quantity of the remainder portion depends on the volume of the measurement cell 406, and the volume of the first portion, in turn, depends on the volume of the remainder portion. At 506, the first portion is dried. For example, the first portion is dried in the drying chamber 408. At 508, the dried first portion is stored in a storage tank, for example, the storage tank 410. At 510, the dried first portion is flowed from the storage tank to a measurement cell, for example, the measurement cell 406. At 512, the split remainder portion is also flowed to the measurement cell.

At 514, the remainder portion and the dried first portion are mixed. The mixing is implemented, for example, in the measurement cell 406. At 516, a water cut of the sample is determined. The water cut can be displayed, for example, on the display device of a computer system. At 518, it is determined if additional samples are to be measured for water content. If additional samples are to be measured (decision branch "YES"), then steps 502, 504, 506, 508, 510, 512, 514, and 516 are repeated to determine the water cuts for multiple respective samples. In particular, each additional sample is drawn from the flowline at a respective time instant, and its water cut is measured. The frequency at which the different samples are drawn and water cut measured can depend upon the operation being performed or the process being controlled. For example, four samples can be drawn and measured periodically, that is, at equal time intervals, each hour. In this manner, water cuts of multiple samples drawn from the flowline over a duration that spans multiple time instants is obtained. If no additional samples remain (decision branch "NO"), then, at 520, a water cut profile of the liquid hydrocarbon is determined. The water cut profile is a plot of water cuts of the multiple samples versus the respective time instants at which the multiple samples were drawn from the flowline 402 or at which the water cut was measured for the multiple samples. The computer system can generate the water cut profile using any plot or graph generation software. At 524, the water cut is displayed on the display device.

In the implementation described with reference to FIGS. 4 and 5, the liquid hydrocarbon sample was drawn from the flowline 402 at a particular height measured from the bottom of the flowline 402. In such an implementation, the water cut of each sample or the water cut profile of multiple samples is representative of the water cut in the liquid hydrocarbon flowing through the flowline 402 at the measured height. In some implementations, the techniques described here can be implemented to determine water cut at different heights in a separation vessel. Recognizing that the water cut can be different at different heights within the vessel, multiple samples can be drawn from the vessel at different heights measured from the bottom of the vessel. By doing so, a water cut profile across a height of the vessel can be determined. Using the water cut or water cut profile (or both) measured as described in this disclosure, a control system can be programmed to create a relationship between water cut, that is, BS&W readings, and certain operations, for example, wash water flow rate, demulsifier flow rate, opening of recirculation valve, heating requirements in the presence of a heat exchanger or similar wellbore, flowline or plant operations. Off-spec crude oil can be segregated and sent to different tanks. In some implementations, a mixing element, for example, a static mixer, can be disposed in the flowline 402 and the hydrocarbon can be sampled downstream of the mixing element to ensure mixing of the hydrocarbons and obtaining a representative sample. In some implementations, the techniques described here can be implemented at a tank farm or a terminal that receives hydrocarbons for shipment. These hydrocarbons can be measured for moisture content using the techniques described here and segregated into different tanks. Off-spec fluids can be directed to storage tanks for water/refined product separation till the fluids become within-spec for offloading. Within-spec fluids can be directed to the tanks where offloading can start without delay.

Example

Figure 6:
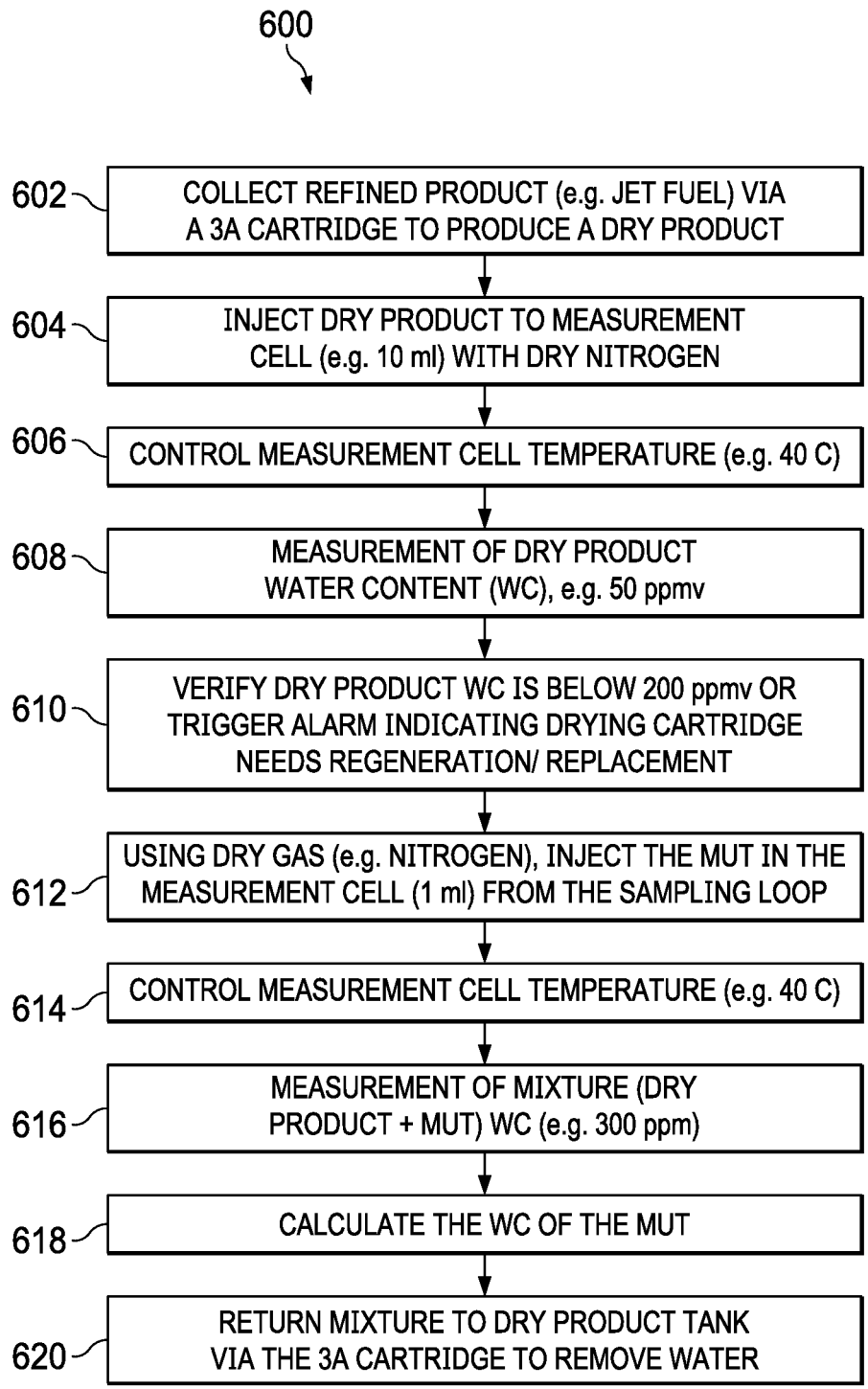
FIG. 6 is a description of an example of another process for measuring water cut in a liquid hydrocarbon sample.

FIG. 6 is a description of an example of another process for measuring water cut in a liquid hydrocarbon sample. At 602, jet fuel was dried by a 3 A cartridge to produce a dry product. At 604, the dried product was injected into a 10 ml measurement cell with dry nitrogen. At 606, the temperature of the measurement cell was controlled at 40° C. At 608, water content in the dried product was measured. The water content was found to be 50 parts per million by volume (ppmv). At 610, it was verified that the dried product water content was below a water content threshold of 200 ppmv. If the dried product water content had been greater than the water content threshold, then an alarm would have triggered requiring replacement of the dried product or the molecular sieve cartridge at the inlet of the dried product storage tank. At 612, 1 ml of jet fuel (that is, the same hydrocarbon that was dried at step 602) was injected from the fast loop system with dry nitrogen into the measurement cell. At 614, a temperature of the measurement cell was maintained at 40° C. At 616, water content of the mixture of the dried product and the jet fuel in the measurement cell was measured to be 300 ppm. At 618, the water cut of the jet fuel was determined. In particular, the water cut of the jet fuel was measured using the following formula:

$$\text{Liquid } HC \text{ } WC = \frac{(mix. \text{ } vol. \times mix. \text{ } WC) - (\text{dried product } vol. \times \text{dried product } WC)}{\text{Liquid } HC \text{ volume}}$$

In the formula above, "liquid HC" stands for the jet fuel, "mix. vol." stands for the volume of the mixture of the jet fuel and the dried product and "mix. WC" stands for the water cut of the mixture. In this example, the liquid HC WC was 2800 ppm or 0.28%. At 620, the mixture was returned to the dried product storage tank to remove water.

In some implementations, the water cut measurement system described here can be calibrated. To do so, two samples can be drawn, either simultaneously or at different time instants. The samples can be diluted differently. For example, the first sample can be diluted at a 1:10 ratio, and the second sample can be diluted at a 1:20 ratio with a dilution fluid, for example, the dried product. The water cut measurement can be implemented for both samples as described earlier. If the system operates as intended, then the water cut of the first sample will be twice that of the second sample. When similar calibration is implemented for multiple samples with a linear range of dilution ratios, the water cut profile for the samples will also be linear. Alternatively or in addition, processing two similar samples but diluted at two different ratio (1:10 ratio and 1:20 ratio for instance) in parallel allows solving a system of two equations with two unknowns (the original water contents in the hydrocarbons and the solvent), enabling measurement of the water content of the mixture components.

In some implementations, the implementations described with reference to FIGS. 1 and 4 can be combined. For example, dry solvent (for example, xylene) can be stored in a first storage tank and dried liquid hydrocarbon sample (for example, dried crude oil) can be stored in a second storage tank. Both storage tanks can be fluidically coupled to the same measurement cell by respective pumps, valves, and fluid flow pathways (for example, pipes or tubes). Combining both implementations in this manner allows using either dry solvent or dried liquid hydrocarbon sample to decrease the concentration of water in the liquid hydrocarbon sample below the saturation level. For example, each storage tank can include a respective sensor that can sense a quantity of the dried product (either dry solvent or dried liquid hydrocarbon sample) in that storage tank, and transmit the quantity to the computer system. If the quantity in the dry solvent storage tank decreases below a threshold quantity level, then the computer system can close the dry solvent storage tank and draw dried product from the dried liquid hydrocarbon sample storage tank, and vice versa. In some implementations, each storage tank can be fluidically coupled to a respective drying chamber that further dries the dried product before the dried product is flowed to the measurement cell. The computer system can monitor a saturation level in each drying chamber. If the saturation level of the drying chamber through which the dried liquid hydrocarbon sample flows is greater than a threshold saturation level, the computer system can close the dried liquid hydrocarbon sample storage tank and draw dried product from the dry solvent storage tank. Doing so allows replacing the drying chamber that is water saturated. In some implementations such as refineries or chemicals production plants handling a variety of products, the system can receive streams from different flow lines and mix these streams with the most suitable solvent (for example, a generic solvent such as xylene or the dried stream or another solvent).

To summarize, the techniques described in this disclosure allow measuring the water content of water-saturated petroleum fluids that contain dispersed droplets. Implementing the techniques enables the water present in the form of droplets in the crude oil to be dissolved in a dry solvent, and hence to be easily measured as part of a homogeneous mixture. By varying the volume ratio of solvent and petroleum fluid, it is possible to cover a very wide range (for example, from 0% to 100%) of water concentrations in a petroleum fluid.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A method comprising:
receiving a liquid hydrocarbon sample from a flowline carrying the liquid hydrocarbon, the liquid hydrocarbon sample comprising liquid hydrocarbon and liquid water at a concentration greater than a water saturation level;
splitting the liquid hydrocarbon sample into a first portion and a remainder portion;
drying the first portion to remove liquid water in the first portion;
mixing the remainder portion with the dried first portion, wherein the concentration of liquid water in a mixture of the remainder portion and the dried first portion is below the water saturation level; and
after mixing the remainder portion with the dried first portion, determining a water content in the liquid hydrocarbon sample.

2. The method of claim 1, further comprising:
transmitting the water content to a computer system; and
displaying the water content on a display device connected to the computer system.

3. The method of claim 1, wherein splitting the liquid hydrocarbon sample into a first portion and a remainder portion comprises:
receiving, by a flow control device, the liquid hydrocarbon sample through a first fluid flow pathway;
flowing, by the flow control device, the first portion into a second fluid flow pathway separate from the first fluid flow pathway; and
flowing, by the flow control device, the remainder portion into a third fluid flow pathway separate from the first fluid flow pathway and the second fluid flow pathway.

4. The method of claim 3, further comprising flowing the remainder portion through the third fluid flow pathway into a measurement cell.

5. The method of claim 4, wherein mixing the remainder portion with the dried first portion comprises flowing the dried first portion into the measurement cell.

6. The method of claim 4, further comprising controlling a temperature of the measurement cell to remain substantially at a temperature before mixing the remainder portion with the dried first portion and during determining the water content of the liquid water in the liquid hydrocarbon sample.

7. The method of claim 6, wherein the temperature is 40° C.

8. The method of claim 4, wherein drying the first portion to remove the liquid water in the first portion comprises flowing the first portion from the second fluid flow pathway through a drying chamber configured to remove the liquid water in the first portion.

9. The method of claim 8, further comprising, before mixing the remainder portion with the dried first portion, flowing the dried first portion from the drying chamber to a storage tank fluidically coupled to the measurement cell to flow the dried first portion from the storage tank to the measurement cell.

10. The method of claim 9, further comprising flowing the mixture of the remainder portion and the dried first portion from the measurement cell to the storage tank.

11. The method of claim 9, further comprising, before mixing the remainder portion with the dried first portion:
determining that a water content of the dried first portion is greater than a water content threshold; and
responsive to determining that the water content of the dried first portion is greater than the water content threshold, transmitting an alarm signal to cease mixing the remainder portion with the dried first portion.

12. A method comprising:
(a) splitting a liquid hydrocarbon sample drawn from a flowline into a first portion and a remainder portion, the liquid hydrocarbon sample comprising liquid hydrocarbon and liquid water at a concentration greater than a water saturation level;
(b) drying the first portion to remove liquid water in the first portion, a quantity of the first portion configured to reduce the liquid water to below the water saturation;
(c) mixing the remainder portion with the dried first portion; and
(d) after mixing the liquid hydrocarbon sample with the dried first portion, determining a water content of the liquid water in the liquid hydrocarbon sample.

13. The method of claim 12, further comprising, before mixing the remainder portion with the dried first portion, drying the dried first portion to decrease water content in the dried first portion.

14. The method of claim 12, wherein steps (a), (b), (c), and (d) are implemented at a first time instant, the method further comprising:
implementing steps (a), (b), (c), and (d) at a plurality of time instants following the first time instant;
determining a plurality of water contents at the plurality of time instants; and
plotting the plurality of water contents versus the plurality of time instants to yield a water cut profile for the liquid hydrocarbon flowed through the flowline during the plurality of time instants.

15. The method of claim 12, further comprising:
transmitting the water content to a computer system; and
displaying the water content on a display device connected to the computer system.

16. The method of claim 12, further comprising flowing the mixture of the dried first portion and the liquid hydrocarbon sample to the flowline.

17. The method of claim 12, further comprising drawing the remaining portion into a measurement cell.

18. The method of claim 17, wherein mixing the remaining portion with the dried first portion comprises:
flowing the dried first portion to a storage tank fluidically coupled to the measurement cell; and
flowing the dried first portion from the storage tank into the measurement cell.

* * * * *